US007826059B2

(12) United States Patent
Roth et al.

(10) Patent No.: US 7,826,059 B2
(45) Date of Patent: Nov. 2, 2010

(54) METHOD AND APPARATUS FOR POLARIZATION-SENSITIVE OPTICAL COHERENCE TOMOGRAPHY

(76) Inventors: Jonathan E. Roth, 1204 Spring Meadow La., Lansdale, PA (US) 19446; Joseph A. Izatt, 10505 Leslie Dr., Raleigh, NC (US) 27615; Andrew M. Rollins, 534 Miner Rd., Highland Hts., OH (US) 44143

( * ) Notice: Subject to any disclaimer, the term of this patent is extended or adjusted under 35 U.S.C. 154(b) by 2280 days.

(21) Appl. No.: 10/055,282

(22) Filed: Jan. 22, 2002

(65) Prior Publication Data

US 2002/0196446 A1    Dec. 26, 2002

Related U.S. Application Data

(60) Provisional application No. 60/263,672, filed on Jan. 22, 2001.

(51) Int. Cl.
    *G01B 9/02*    (2006.01)
(52) U.S. Cl. ............... 356/450; 600/473; 600/476; 356/451; 356/453; 356/364
(58) Field of Classification Search ............... 356/450, 356/453, 364
    See application file for complete search history.

(56) References Cited

U.S. PATENT DOCUMENTS 5,684,545 A * 11/1997 Dou et al. ............... 349/1

FOREIGN PATENT DOCUMENTS

WO    WO00/69333    * 11/2000
WO    WO0069333 A    11/2000

OTHER PUBLICATIONS

Podoleanu A.G. et al: "Simultaneous En-Face Imaging of Two Layers in the Human Retina by Low-Coherence Reflectometry", Optics Letters, Optical Society of America, Washington, US, vol. 22, No. 13, Jul. 1, 1997, pp. 1039-1041, XP000658709.
Podoleanu A.G. et al: "Simultaneous Low Coherence Interferometry Imaging At Two Depths Using an Integrated Optic Modulator", Optics Communications, North-Holland Publishing Co., Amsterdam, NL, vol. 191, No. 1-2, May 1, 2001, pp. 21-30, XP004234990.
Everett M.J. et al:"Non-invasive Diagnosis of Early Caries With Polarization Sensitive Optical Coherence Tomography", Proceedings of the SPIE, SPIE, Bellingham, VA, us, vol. 3593, Jan. 24, 1999, pp. 177-182, XP000931184, Chapter 3, pp. 178-179, Figure 1.
Boer De J.F. et al: "Polarization Effects in Optical Coherence Tomography of Various Biological Tissues", IEEE Journal of Selected Topics in Quantum Electronics, IEEE Service Center, US., vol. 5, No. 4, Jul. 1999, pp. 1200-1203, XP00893469, Chapter III, pp. 1200-1201, Figure 1.

* cited by examiner

*Primary Examiner*—Brian Casler
*Assistant Examiner*—John F Ramirez

(57) ABSTRACT

A method and apparatus for extracting the vector optical properties of biological samples with micron-scale resolution in three dimensions, using polarization-sensitive optical coherence tomography (PS-OCT). The method measures net retardance, net fast axis, and reflectivity. Polarization sensing is accomplished by illuminating the sample with at least three separate polarization states, using consecutive acquisitions of the same pixel, A-scan, or B-scan. The method can be implemented using non-polarization-maintaining fiber and a single detector. This PS-OCT method reported measures fast axis explicitly. In a calibration test of the system, net retardance was measured with an average error of 7.5° (standard deviation 2.2°) over the retardance range 0° to 180°, and fast axis with average error of 4.8° over the range 0° to 180°.

12 Claims, 3 Drawing Sheets

METHOD AND APPARATUS FOR POLARIZATION-SENSITIVE OPTICAL COHERENCE TOMOGRAPHY

Priority of application No. 60/263,672 filed Jan. 22, 2001 is claimed under 35 USC 119(e).

TECHNICAL FIELD

The present invention relates to optical coherence tomography and, more particularly to polarization-sensitive optical coherence tomography.

BACKGROUND

Optical coherence tomography (OCT) is an emerging technique for in-vivo microscopy which obtains micron-scale cross-sectional images of subsurface structure in biological tissues. While conventional OCT measures the depth-resolved reflectivity profile of backscattered light, polarization-sensitive OCT (PS-OCT) systems have been developed to add the capability of controlling the polarization state of light incident upon the sample and measuring the reflectivity of light returning in particular polarization states. See, for example, M. R. Hee, D. Huang, E. A. Swanson and J. G Fujimoto, J. Opt. Soc. Am. B 9, 903 (1992); and J. F. de Boer, T. E. Milner, M. J. C. van Gemert and J. S. Nelson, Opt. Lett. 22, 934 (1997), the entire disclosures of which hereby are incorporated by reference. Such selectivity allows for the measurement of birefringence and/or dichroism. Prior studies in biological samples have found the effects of dichroism to be minimal in skin and muscle tissue, and have focused on measurement of retardation due to birefringence for contrasting different types of tissue and assessing the severity of burns. See, for example, C. E. Saxer, J. F. de Boer, B. H. Park, Y. Zhao, Z. Chen and J. S. Nelson, Opt. Lett. 25, 1355 (2000); J. F. de Boer, T. E. Milner and J. S. Nelson, Opt. Lett. 24, 300 (1999); and K. Schoenenberger, B. W. Colston, D. J. Maitland, L. B. Da Silva and M. J. Everett, Appl. Opt. 37 6026 (1998), the entire disclosures of which hereby are incorporated by reference. PS-OCT systems also avoid polarization artifacts which occur in conventional OCT images of birefringent samples. See, for example, M. J. Everett, K. Schoenenberger, B. W. Colston and L. B. Da Silva, Opt. Lett. 23, 228 (1998), the entire disclosure of which hereby is incorporated by reference.

Most conventional OCT systems use non-polarization-maintaining (PM) single-mode fiber interconnections because they are inexpensive, allow for easy alignment and handling, and enable flexible sample arm designs which are important for in vivo measurements such as surgical and endoscopic applications. Single-mode optical fiber, however, exhibits undesirable static and dynamic polarization effects due to fiber imperfections, fiber bending, and temperature fluctuations. Most prior PS-OCT systems have been implemented in bulk optics due to the difficulty of maintaining predictable polarization in conventional fibers, and have employed dual orthogonally polarized detection channels. Recently, a conventional-fiber based PS-OCT system has been reported which depends upon the assumption that the non-PM fiber is lossless. See C. E. Saxer, J. F. de Boer, B. H. Park, Y. Zhao, Z. Chen and J. S. Nelson, Opt. Lett. 25, 1355 (2000), which also is identified above.

BRIEF SUMMARY

Briefly, according to an aspect of the invention, a PS-OCT method is implemented with a modification of a conventional fiber-optic OCT interferometer.

Another aspect of the invention relates to a method of retrofitting an OCT interferometer for PS-OCT use.

According to another aspect, the invention bypasses the problem of polarization maintenance in optical fibers by implementing the entire polarization-sensitive apparatus in the sample arm of the OCT interferometer.

According to another aspect, while a conventional non-PS OCT system creates tomographic images by measuring every point once, the present invention takes one or more measurements and finds one or more respective variables, such as, reflectance (as in standard OCT), sample retardance, and sample fast axis.

According to another aspect, while a conventional non-PS OCT system creates tomographic images by measuring every point once, the present invention takes a triple measurement and finds three variables, reflectance (as in standard OCT), sample retardance, and sample fast axis.

According to another aspect, a conventional fiber-optic OCT system can be retrofitted by the addition of hardware parts to perform polarization sensing.

According to another aspect, a conventional fiber-optic OCT system can be retrofitted by the addition of two or more hardware parts to perform polarization sensing.

According to another aspect, a system according to the invention uses a minimum number of components to accomplish the polarization sensing because it encodes the polarization data in the signal amplitude, instead of maintaining the polarization state of light leaving the sample through the interference and detection stages.

Another aspect relates to use of a series of measurements to minimize the components in a PS-OCT system.

According to another aspect, a PS-OCT system can also cancel out artifacts caused by dichroism.

Another aspect relates to an interferometer system having polarization sensitivity, including a reference arm providing a delay line for electromagnetic energy, a sample arm providing a path for incident electromagnetic energy having prescribed polarization characteristics to a sample, and a detector arranged to detect electromagnetic energy from the delay line and from the sample.

Another aspect relates to a retrofit apparatus for making an optical coherence tomography (OCT) system polarization sensitive, comprising a polarizer and a polarization adjusting device positionable in the sample arm of the OCT system.

Another aspect relates to a method of retrofitting an optical coherence tomography (OCT) system for polarization sensitivity, comprising inserting in the sample arm of the OCT system a polarization state determining apparatus.

Another aspect relates to a method of making polarization sensitive optical coherence tomography measurements, including directing light from a source in a delay line and to a sample while selectively determining the polarization state of light directed to the sample, combining light received from the delay line and light from the sample, and detecting the combined light.

Another aspect relates to a method to present measured data from OCT including using an HSV color scale such that three parameters are used and plotted, whereby reflectance is mapped into saturation and value and retardance is mapped into hue.

These and other objects, aspects, features and advantages will become more apparent as the following description proceeds.

A number of features are described herein with respect to embodiments of the invention; it will be appreciated that features described with respect to a given embodiment also may be employed in connection with other embodiments.

The invention comprises the features described herein, including the description, the annexed drawings, and the claims, which set forth in detail certain illustrative embodiments. These embodiments are indicative, however, of but a few of the various ways in which the principles of the invention may be employed.

It will be appreciated that the features and principles of the invention may be used in systems other than those disclosed herein for PS-OCT and the like.

Although the invention is shown and described with respect to illustrative embodiments, it is evident that equivalents and modifications will occur to those persons skilled in the art upon the reading and understanding hereof. The present invention includes all such equivalents and modifications and is limited only by the scope of the claims.

DESCRIPTION

Figure 1:
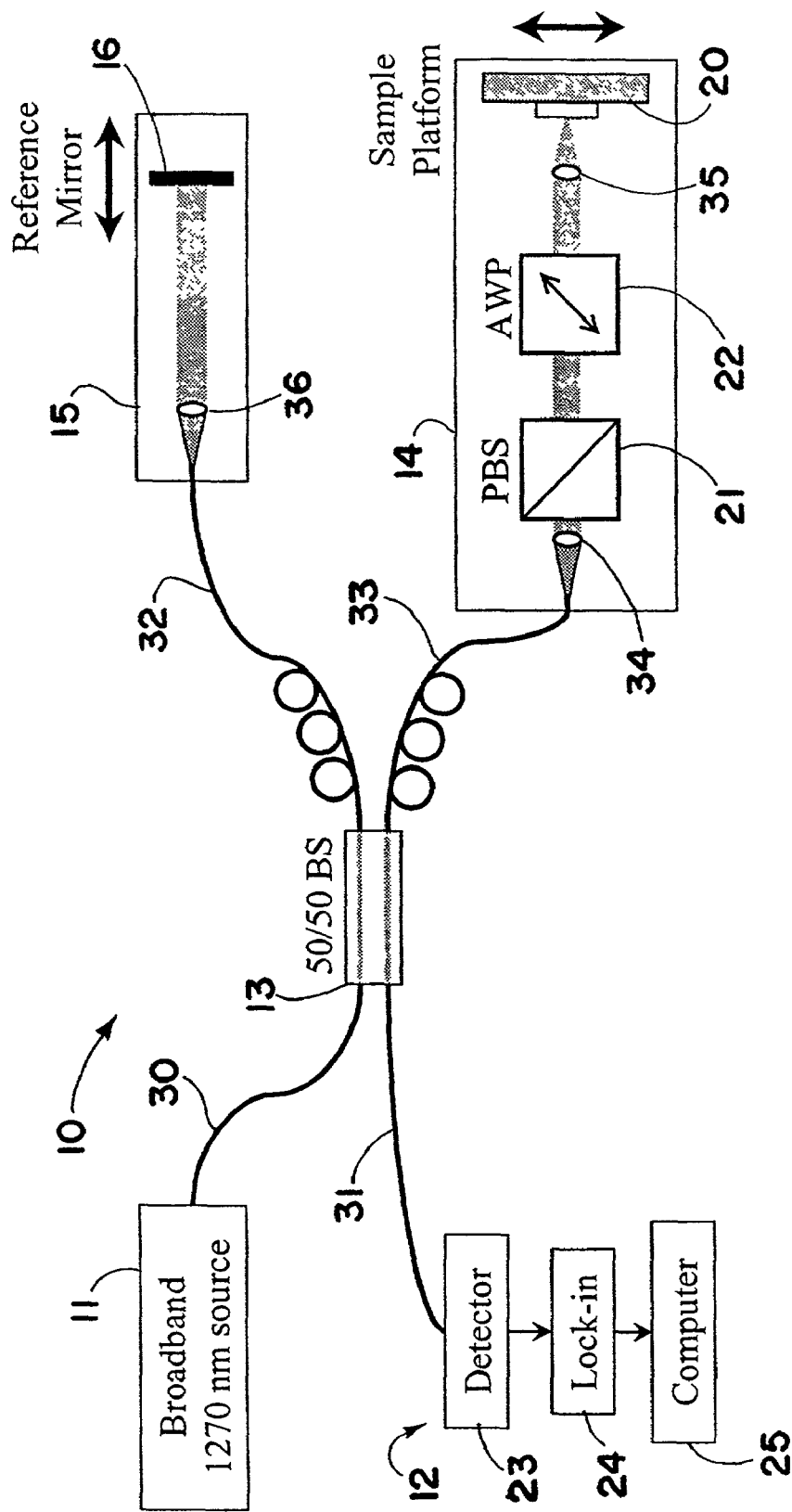
FIG. 1 is a schematic illustration of a polarization-sensitive optical coherence tomography system.

Referring to the drawings, wherein like reference numerals designate like parts in the several figures, and initially to FIG. 1, a polarization-sensitive optical coherence tomography system 10 (sometimes referred to below as PS-OCT or PS-OCT interferometer system) is illustrated. In the schematic diagram of FIG. 1 the PS-OCT system 10 includes a polarizing beam splitter (PBS) passing vertically polarized light and an addressable waveplate (AWP) with fast axis oriented at 45°. These are described further below.

The PS-OCT system 10 includes a source 11, detector apparatus 12, beamsplitter 13, sample arm 14 and reference arm 15. The reference 16 in the reference arm is shown as a mirror; it may be a silvered mirror or some other mirror that is perpendicular to the incident light or is otherwise arranged to receive incident light and to reflect the light back toward the detector apparatus 13. If desired, the reference 16 may be a scanning reflector, a retroreflector or a Fourier domain rapid scan optical delay line. Sometimes the reference arm in an OCT system is referred to as a delay line. It will be appreciated that other configurations of delay lines that ultimately sends the light back into the interferometer may be used.

Using the PS-OCT system 10, at least three separate incident polarization states of light are used to illuminate the sample 20 in the sample arm 14 sequentially, and for each incident polarization, the component of remitted light returning in the same polarization state is measured by the detector apparatus 12. The polarization states may be applied during repeated measurements at the same pixel location, or during repeated line (A-scan) or image (B-scan) acquisitions. From the interference measurements obtained with different polarization states, the total reflected power, net retardance (with $\pi$ ambiguity), and net fast axis (with $\pi/2$ ambiguity) are calculated. In addition to being feasible in conventional fibers without any limitations on flexible sample arm 14 motion (so long as the sequential polarization measurements are acquired quickly with respect to such motion), this approach also obviates the need and expense for dual detection channels.

If desired, more than three polarization states may be used, e.g., the system 10 may be used to examine (sometimes referred to as to probe) a sample using incident light of more than three polarization states. An advantage to taking measurements at more than three polarization states is that the $\pi$ ambiguity and/or the $\pi/2$ ambiguity could be removed.

In an example of PS-OCT system 10 illustrated in FIG. 1, the source 11 is a broadband SLD source centered at 1270 nm with a coherence length of 20.3 µm. Other suitable sources may be used; examples include those having 30 nm, 60 nm, or 70 nm bandwidth or some other suitable bandwidth. The components and arrangement of components of the system 10 are substantially identical to conventional OCT systems with a number of exceptions, some of which are noted below. One of those exceptions is that the sample arm 14 beam is directed through a linear polarizer 21, which is followed by an addressable waveplate 22. An example of an addressable waveplate is a liquid crystal modulator, which may be obtained from Thor Labs, Inc. Another example is an electro-optic phase modulator acting as an addressable waveplate, which usually has a faster response than a liquid crystal modulator. Other devices and/or systems may be used equivalently to provide the function of the addressable (or otherwise adjustable) waveplate 22. An exemplary polarizer is a plane polarizer, such as a polarizing beamsplitter; but other polarizers may be used. The waveplate 22 has its fast axis oriented at 45° with respect to the polarizer. The objective is to illuminate the sample 20 with illumination at a series of polarization states and to measure only the light coming back in the respective polarization state. Changing the setting or optical characteristics of the addressable waveplate 22 during operation of the system 10 adjusts or changes the polarization states of the illumination used to probe the sample, 20. It will be appreciated that components other than the polarizer and addressable waveplate may be used to accomplish such illumination function, e.g., a single polarization determining or adjusting device or a series of components making up the polarization determining or adjusting device.

In a different configuration of interferometer, such as a Mach-Zehnder interferometer, it also is possible to illuminate the sample with one or more polarization states or even virtually an infinite number of polarization states, and the results can be detected in a different channel or path from the incident path.

In one embodiment, fiber polarization adjustors (paddles) 14a, 15a may be used in both the sample and reference arms 14, 15. In another embodiment, (as recited in originally filed claim 6 and illustrated in originally filed figure one), the reference arm 15 is absent polarization adjusting components 14a and 15a.

The detector apparatus 12 may be a photosensitive detector 23, such as a photosensitive diode or other device. The detector apparatus also may include appropriate signal amplifying and/or measuring circuitry, for example, such as are used in conventional optical coherence tomography devices, to provide signals representative of detection by the photosensitive detector. The detector apparatus 12 also may include a signal processing circuit or module, such as an electronic circuit, a lock-in amplifier 24 and a computer 25 as are schematically illustrated. The computer is able to carry out various data storage and data processing functions, such as, for example, those described below. The beamsplitter 13 may be a 50/50 beamsplitter or some other ratio splitter. The optical source may be other than a broadband 1270 nm source, if desired, as will be appreciated. The respective lines 30-33 in FIG. 1 are fiber optic lines or conductors, for example. One or more lenses, such as lenses 34, 35, 36 illustrated in FIG. 1 may be used to provide various focusing effects at the sample and reference arms 14, 15 and/or elsewhere in the system 10.

In the example below particular orientation (e.g., 45 degrees) and operation of components in the sample arm 14, e.g., linear polarizer 21 and addressable waveplate 22 are described. It will be appreciated that these are exemplary, and that other components, arrangements and operation could be used consistent with the invention disclosure, e.g., to generalize the components and their use in a PS-OCT system, such as in the system 10. For example, although the mathematics may be more complex what is described in the example below, orientation of axes other than at the 45° relation described could be used; the angular relationships between polarization states could be equal or unequal, etc., thus generalizing the light directions and/or polarization states described.

Adding to the sample arm 14 a linear polarizer 21 and addressable waveplate 22 with axes oriented 45° apart causes attenuation of remitted light in the sample arm as a function of the addressable waveplate retardance (r), the net sample retardance accumulated to the depth being examined ($\delta$), and the net sample fast axis angle to that depth ($\theta$). The power of remitted sample arm 14 light at the detector apparatus 12 after a round trip through the polarizing optics is given by:

$$P_s^{pol}(r) = P_s \cdot \left[ \frac{1}{2} + \frac{1}{2}\cos^2(r) \cdot (\cos^2(2\theta) + \sin^2(2\theta)\cos(\delta)) - \cos(r)\sin(r)\sin(2\theta)\sin(\delta) - \frac{1}{2}\sin^2(r)\cos(\delta) \right], \quad (1)$$

where $P_s$ is the optical power at the receiver remitted from the sample location in all polarization states, proportional to the total sample reflectivity at a given depth. The amplitude of the envelope of the OCT signal photocurrent is given by $A_{is}=2\rho\sqrt{P_rP_s}$, where $\rho$ is the detector responsivity, and $P_r$ is the optical power incident on the receiver or detector apparatus 12 returning from the reference arm 15 of the interferometer 30 of the PS-OCT system 10. See, for example, A. M. Rollins and J. A. Izatt, Opt. Lett. 24, 1484 (1999), the entire disclosure of which is hereby incorporated by reference. By measuring sequential PS-OCT pixels, A- or B-scans with three or more addressable waveplate settings r, corresponding values of $A_{is}^{pol}(r)=2\rho\sqrt{P_rP_s^{pol}(r)}$ can be measured, and the three unknown quantities ($A_{is}^2 \propto P_s, \delta, \theta$) can be extracted from the three measurements by algebraic manipulation. The term $A_{is}^2$ is measured—it is the response of the optical detector; it is proportion to the optical power on the detector and, thus, is proportional to the reflectivity of the sample. The unknown quantity "$A_{is}^2 \propto P_s$" is used because the actual parameter in Equation 1 is the optical power. The term $\delta$ refers to retardation, and the term $\theta$ refers to the fast axis direction or angular relation. For three incident polarizations obtained using addressable waveplate 22 retardations of 45°, 90°, and 135°, the expressions are:

$$A_{is}^2 = \frac{1}{2}(A_{45}^2 + A_{135}^2) + \frac{1}{2}\sqrt{(A_{45}^2 + A_{135}^2 - 2A_{90}^2)^2 + (A_{45}^2 - A_{135}^2)^2}\,; \quad (2)$$

$$\delta = \cos^{-1}\left(1 - \frac{2 \cdot A_{90}^2}{A_{is}^2}\right);$$

$$\theta = \frac{1}{2}\sin^{-1}\left[\frac{A_{135}^2 - A_{45}^2}{A_{is}^2 \cdot \sqrt{1 - (1 - 2A_{90}^2/A_{is}^2)^2}}\right].$$

In these expressions, $A_r$ represents $A_{is}^{pol}(r)$, the amplitude of the envelope of the interferogram at a given depth measured with an addressable waveplate retardance of r°. Equation 1 is written in terms of $P_s$ for conceptual simplicity, while equations 2 are written in terms of $A_{is}$ (the measured quantity) in order to be directly applicable to experimental measurements.

Figure 2:
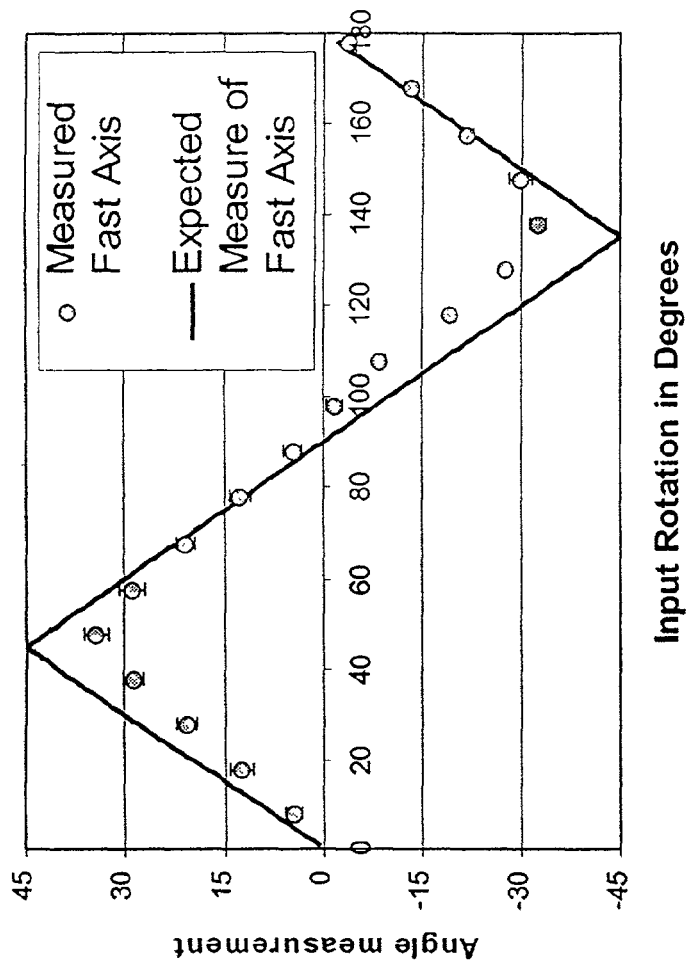
FIG. 2(a) is a graphical representation of measured vs. actual retardation in a calibrated test plate used in the system of the invention.
FIG. 2(b) is a graphical representation of measured vs. predicted fast axis in a calibration test sample used in the system of the invention.
Figure 2:
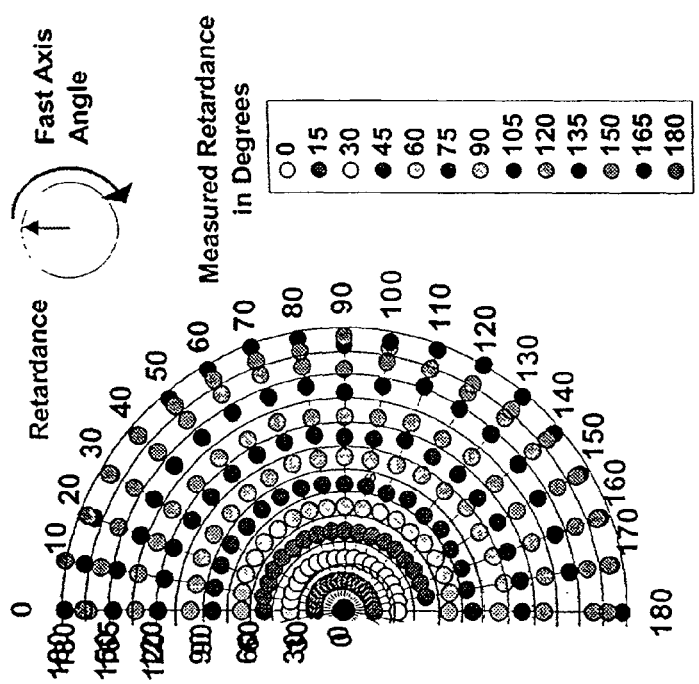

The accuracy of the system 10 was tested by measuring the retardation of a calibrated Berek polarization compensator, which is available from New Focus, Inc., over the range of 0° to 180° of retardation in 15° increments, and 0 to 180° fast axis angle in 10° increments. For each sample birefringence setting, 20 PS-OCT A-scans were averaged at each addressable waveplate 22 setting of°, 90°, and 135°, These waveplate positions were chosen to fall within the retardance range of the addressable waveplate, and to maximize or minimize the three terms in equation (1) which may be separated to calculate quantities $P_s, \delta$, and 74. The calibration results presented in FIG. 2(a) demonstrate an average error of 7.5° in retardation measurements (26.5 nm average retardance error), including a systematic error which is approximately linear with sample 20 retardance. The average standard deviation of the measured retardation was 2.2°, corresponding to 7.8 nm of retardance repeatability error. The systematic error may be due to incorrect factory calibration of the Berek compensator test plate. The fast axis is read out on a 90° scale, with a result mapping to 2 points in the range of fast axis from 0° to 180° (due to the $\pi/2$ ambiguity in fast axis determination). As illustrated in FIG. 2(b), this reading has an average error of 4.8°, and each value maps to 2 possible physical axis locations.

As was mentioned above, the example presented uses 45 degrees separations. However, other separations may be used, e.g., 60 degrees or some other amount; and, if desired the separations may be "equidistant" or unequal. The settings/values mentioned could be any arbitrary value to extract the mentioned three parameters, although the mathematics may be more complex than for the example presented above. These three settings were used as a matter of convenience due to the limitations of the liquid crystal wave plate that was used in the exemplary system presented; but in general, the principles of the invention are not limited to such settings.

In FIG. 2(a) measured vs. actual retardation in a calibrated test plate is illustrated. Solid rings represent the test plate retardation settings in degrees, and the data points represent measured retardation settings. The angle from the origin represents the fast axis setting, from 0° to 180°.

In FIG. 2(b) measured vs. predicted fast axis in the calibration test sample is illustrated. The horizontal axis represents the fast axis. The solid lines represent the test plate fast axis settings, and points represent the measured fast axis orientation. The fast axis readings represent averaged acquisitions; each reading corresponds to 2 possible fast axis locations.

In an example of use of the system 10, the depth-resolving capability of birefringence detection in this system 10 was tested by placing the Berek's variable waveplate in series with a fixed waveplate of 57.1° retardation at the same fast axis angle. The measured retardation of the fixed plate was measured for variable waveplate retardations of −15°, −5°, 0°, 5°, 15° and 30°. The average error in the measurement of retardation in the fixed waveplate was 1.2°.

Figure 3:
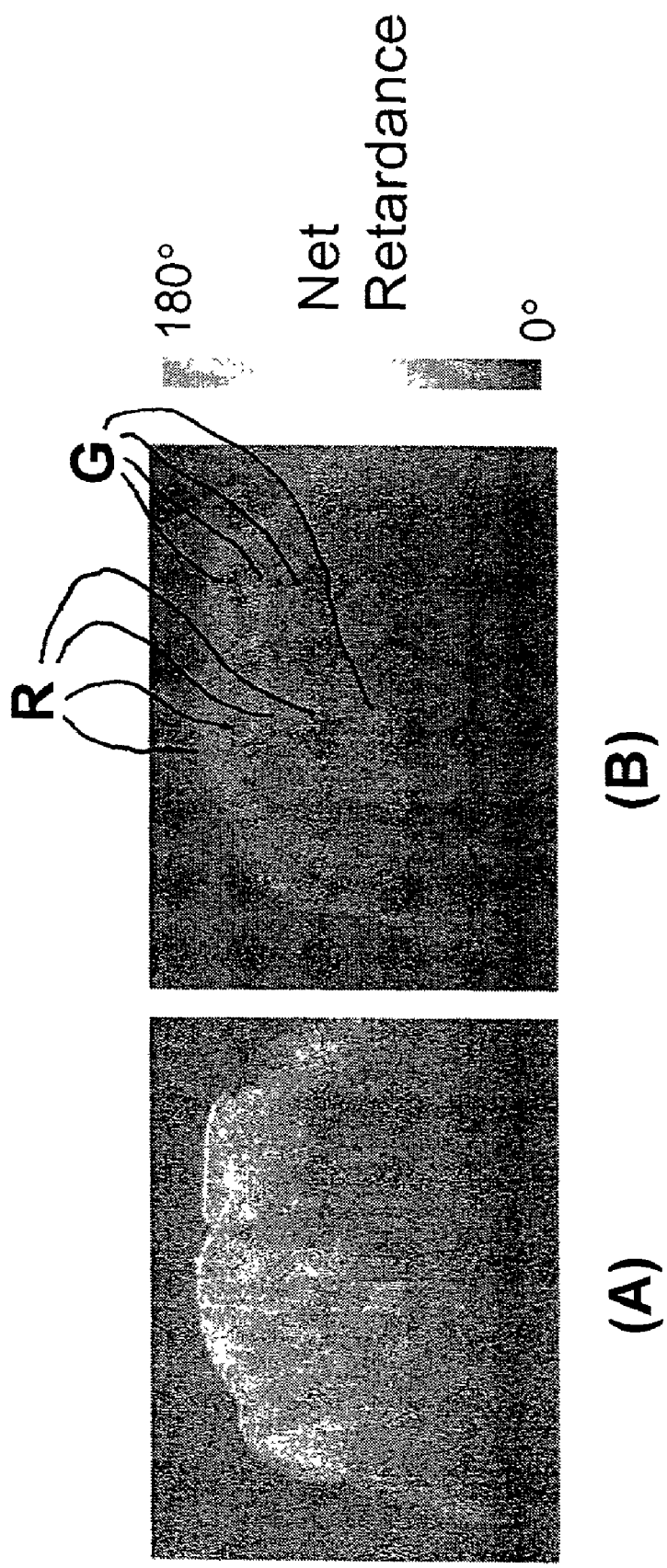
FIG. 3(a) is a polarization-sensitive OCT image of ex vivo Xenopus laevis leg muscle, the left image representing optical power reflectivity image plotted on a logarithmic scale.
FIG. 3(b) is a polarization-sensitive OCT image of ex vivo Xenopus laevis leg muscle representing combined retardation/optical power presented with a hue-saturation value (HSV) color scale.

In another example of use of the system 10, to illustrate the performance of the system 10 in biological media, the PS-OCT system 10 was used to image a cross section of muscular tissue from the hind leg of an ex vivo Xenopus laevis African tadpole. For this experiment, three sequential images each comprising 400 A-scans were obtained at addressable waveplate settings of 45°, 90°, and 135°. The total image acquisition time was 6 minutes. FIGS. 3(a) and 3(b) illustrate the resulting images of total reflected optical power (FIG. 3(a)) and of combined reflectivity and birefringence (FIG. 3(b)). The birefringence image is presented on a hue-saturation-value (HSV) color scale, with power ($P_s \propto A_{is}^2$) coded as the value and saturation components, and retardance ($\delta$) coded as the hue. Each red band, which is labeled with the letter "R" in the image, represents a net retardance of an integral number of optical periods, while each green band, which is labeled with the letter "G" in the image, represents a halfwave offset.

In FIGS. 3(a) and 3(b) Image dimensions are 6 mm wide by 4.5 mm deep. In FIG. 3(a) optical power reflectivity image is plotted on a logarithmic scale. FIG. 3(b) is a combined retardation/optical power image. On the hue-saturation-value (HSV) color scale in FIG. 3(b), reflected optical power is displayed in saturation and value, and retardance is displayed in hue. The hue color scale is displayed at the right, representing net retardance of 0° in red (designated by the letter "R") and of 180° in green (designated by the letter "G"). A useful way to plot the data is to use an HSV color scale such that the three parameters are used and plotted, whereby reflectance is mapped into saturation and value and retardance is mapped into hue.

It will be appreciated that the invention relates to a non-polarization maintaining (non-PM) fiber based polarization-sensing optical coherence tomography system with a single detector apparatus 12, which relies on temporally multiplexed illumination of the sample 20 with at least three different polarization states for determination of depth-resolved sample birefringence, net fast axis, and total reflectivity. Using this approach, conventional fiberbased OCT systems may be inexpensively retrofitted for polarization-sensitive measurements.

The PS-OCT system 10 and method described above measure the effects of birefringence in a sample 20. In the technique presented it is desirable and may be required that dichroism, another polarization-sensitive effect, not be present. If dichroism were suspected, a technique employing six measurements of the sample instead of three could be employed to cancel out dichroism or to measure dichroism. Thus, this is an example of utility of making more measurements using the principles of the present invention.

In equation (1) above the attenuation experienced at the linear polarizer 21 is described as a function of the retardation and fast axis of the sample 20 and the retardation of the variable waveplate 22. The dependence on waveplate retardation has a 180 degree period, while the range of possible polarization states incident on the sample are created over 360 degrees of retardation at the waveplate. Therefore, in the presence of only birefringence effects, two settings of the variable waveplate 180 degrees apart will have equal attenuation at the linear polarizer 21, as is described in equation (4) below and will cause orthogonal polarization states of light incident upon the sample 20, as is described in equation (5) below.

$$I_{pol} = I \cdot \left[\frac{1}{2} + \frac{1}{2}\cos^2(r) \cdot (\cos^2(2\theta) + \sin^2(2\theta)\cos(\delta)) - \cos(r)\sin(r)\sin(2\theta)\sin(\delta) - \frac{1}{2}\sin^2(r)\cos(\delta)\right] = I \cdot \left[\frac{1}{2} + \frac{1}{2}\cos^2(r+\pi) \cdot (\cos^2(2\theta) + \sin^2(2\theta)\cos(\delta)) - \cos(r+\pi)\sin(r+\pi)\sin(2\theta)\sin(\delta) - \frac{1}{2}\sin^2(r+\pi)\cos(\delta)\right] \quad (4)$$

Polarization state of light incident upon sample 20:

$$\begin{bmatrix} 1 & 0 & 0 & 0 \\ 0 & \cos r & 0 & -\sin r \\ 0 & 0 & 1 & 0 \\ 0 & \sin r & 0 & \cos r \end{bmatrix} \cdot \begin{bmatrix} 1 \\ -1 \\ 0 \\ 0 \end{bmatrix} = \begin{bmatrix} 1 \\ -\cos r \\ 0 \\ -\sin r \end{bmatrix} \quad (5)$$

Two beams are orthogonal if they are related as a) and b):

$$a) \begin{bmatrix} A \\ B \\ C \\ D \end{bmatrix} \quad b) \; c \cdot \begin{bmatrix} A \\ -B \\ -C \\ -D \end{bmatrix}$$

The polarization states incident upon the sample 20 from variable waveplate 22 settings $r$ separated by 180 degrees are orthogonal.

If dichroism is not present in the sample 20, adding 180 degrees to the retardation at the variable waveplate 22 will not change the measurement. If dichroism is present, these two values may be different and can be averaged to yield a dichroism independent result.

Recognizing that a waveplate will not affect whether two incident beams are orthogonal: Their orthogonality or non-orthogonality will be preserved through the waveplate 22. A dichroic reflection in the sample 20 can be modeled by summing the transition through two orthogonal linear polarizers with different attenuation coefficients, as described in equation (6) below, with c1 and c2 equal to cos(2*d), where d describes the axis of dichroism. R1 and R2 are reflectivities along 2 axes. I describes the input light.

$$R(I) = R1 \cdot 1/2 \cdot \begin{bmatrix} 1 & c2 & s2 & 0 \\ c2 & c2^2 & c2s2 & 0 \\ s2 & c2s2 & s2^2 & 0 \\ 0 & 0 & 0 & 0 \end{bmatrix} \cdot [I] + \qquad (6)$$

$$R2 \cdot 1/2 \cdot \begin{bmatrix} 1 & -c2 & -s2 & 0 \\ -c2 & c2^2 & c2s2 & 0 \\ -s2 & c2s2 & s2^2 & 0 \\ 0 & 0 & 0 & 0 \end{bmatrix} \cdot [I]$$

If two orthogonal states of input light are used, $$\begin{bmatrix} I1 \\ I2 \\ I3 \\ I4 \end{bmatrix}, \text{ and } \begin{bmatrix} I1 \\ -I2 \\ -I3 \\ -I4 \end{bmatrix},$$

the two resulting intensities of reflectivity will be:

$R(I) = R1 \cdot \frac{1}{2} \cdot (I1 + I2c2 + I3s2) + R2 \cdot \frac{1}{2} \cdot (I1 - I2c2 - I3s2)$ and $R(I') = R1 \cdot \frac{1}{2} \cdot (I1 - I2c2 - I3s2) + R2 \cdot \frac{1}{2} \cdot (I1 + I2c2 + I3s2).$ The average of R(I) and R(I') is $$\frac{I1 \cdot (R1 + R2)}{2},$$

a result independent of the axis of dichroism.

To use these results in the PS-OCT system 10, each of the three measurements will be replaced by an average of two measurements with variable waveplate settings 180 degrees apart. This method may be effective in application in making measurements in tissue. Below a strong dichroic layer in the tissue, the ability of the system 10 to measure retardation or cancel dichroism on another axis will be impaired, as it will not be practically possible to control the state of polarization of light incident on those deeper regions of tissue. It may be desirable to measure the difference between the averaged signal pairs to measure the dichroism present, so the user might know that birefringence measurements beneath that region be of decreased accuracy.

From the foregoing, it will be appreciated that the present invention may be used to provide in an OCT system the ability and functions of a PS-OCT system by inserting in the sample arm components to provide for illumination of the sample at a selected number of polarization states, e.g., two or more polarization states. Measurements may be made at the respective polarization states, whereby the remitted light (or other illumination/electromagnetic energy) measured is at the same polarization state as that incident on the sample to probe the sample. In other interferometer embodiments, e.g., Mach-Zehnder type or other type, the state detected at the detector may be different than the polarization state incident on the sample. In the illustrated embodiment there are two components added in the sample arm, namely the polarizer and the addressable waveplate; but there may be other components to provide the described functions. The number of settings of the components added in the sample arm may be the described three but may be more or less than three to provide a corresponding number of polarization states.

The system 10 may be considered a time multiplexed system in which polarization encoding is done by taking several measurements one after another, e.g., sequentially. Accordingly, by easily retrofitting into the sample arm 14 the polarization components, e.g., the polarizer 21 and waveplate 22, and coordinating the measurements so they are taken sequentially one after another in coordinated relation with the polarization state of incident illumination probing the sample 20 a standard OCT can be converted to a PS-OCT. Also, by placing the optical components dealing with optical polarization characteristics in one place, e.g., in the sample arm 14, rather than having such components in different places in the system 10, it is not necessary to use polarization preserving options in other parts of the interferometer.

Using the features of the present invention the polarization components, e.g., the polarizer 21 and the waveplate 22 need be only in the sample arm and, thus, only a single detector 12 is needed to obtain measurements at different respective polarization states.

As was mentioned above, the taking of fewer measurements than the measurements at three respective polarization states is possible, although the number of parameters measured would decrease than the three described at the three polarization states described.

However, as also was mentioned above, the number of polarization states at which measurements are taken could be more than three and, accordingly, more parameters could be measured and/or measurements of parameters could be of improved accuracy as the number of polarization states and measurements is increased. Examples of parameters include not only retardation and fast axis angle, but also measurements of layers, e.g., if the sample 20 had several layers, each with its own retardance and/or thickness characteristics. Dichroism is another parameter that could be measured, as also was mentioned above; for example, dichroism may result when one polarization state is absorbed more than another polarization state.

By reducing the number of components required to obtain the PS-OCT functions, namely for polarization sensitivity, whereby as few as two components, e.g., the linear polarizer 21 and waveplate 22, or their equivalent, and placing the same in the sample arm many existing conventional OCT systems can be retrofitted easily to provide the PS function.

As is described above, the invention may be used to take three successive measurements or readings at three successive polarization states, and the measurements could be made on lines, pixels, etc. However, it will be appreciated that consistent with the invention the polarization state could be continuously modulated. The modulation could be done according to a ramp function, a sawtooth function, a sinusoidal function, or in discrete steps, or in any other manner. The signal, e.g., the remitted light from the sample 20, can be measured in coordinated relation with the modulation function and the various parameters or values for those parameters that are to be extracted from the measurements can be obtained. As an example, the waveplate 22 could be modulated sinusoidally with a signal generator; and at the detector, the detected signal would be coordinated with the signal from the signal generator so that the measurements are made, for example, synchronously with the driving waveform of the signal generator.

INDUSTRIAL APPLICATION

It will be appreciated that the invention may be used in the making of optical measurements. The invention also may be used to retrofit OCT systems for PS-OCT functions.

We claim:

1. An interferometer apparatus comprising:
a reference arm providing a delay line for a first electromagnetic energy, the first electromagnetic energy being light, where the reference arm is absent addressable polarization selecting components;
a sample arm providing a path for an incident electromagnetic energy to a sample, the incident electromagnetic energy being light, the incident electromagnetic energy being associated with the first electromagnetic energy, the incident electromagnetic energy having prescribed polarization characteristics, the sample arm including a polarization adjusting device to control the prescribed polarization characteristics; and
a detector arranged to detect electromagnetic energy from the delay line and to detect light remitted from the sample,
where the interferometer apparatus is to illuminate the sample with illumination at a series of polarization states and to measure light remitted from the sample according to the series of polarization states.

2. The interferometer apparatus of claim 1, comprising a beamsplitter directing light from a source to the reference arm and to the sample arm and for combining light from the reference and sample arms to direct the combined light to the detector.

3. The apparatus of claim 1, where to measure light remitted from the sample according to the series of polarization states comprises measuring birefringence.

4. The apparatus of claim 1, where the polarization adjusting device comprises an adjustable waveplate and a linear polarizer.

5. The apparatus of claim 1, where to measure light remitted from the sample according to the series of polarization states comprises measuring fast axis orientation.

6. The apparatus of claim 1, where the detector comprises a photosensitive detector, a lock-in device and a computer for analyzing signals detected by the detector.

7. The apparatus of claim 1, comprising a drive for determining the polarization states of incident electromagnetic energy directed to the sample and detected by the detector.

8. An interferometer system having polarization sensitivity, comprising:
a reference arm providing a delay line for electromagnetic energy, where the reference arm is absent addressable polarization selecting components;
a sample arm providing a path for incident electromagnetic energy having prescribed polarization characteristics to a sample, said sample arm including a polarizer and a polarization adjusting device that is selectively operable to modulate polarization; and
a detector arranged to detect electromagnetic energy from the delay line and from the sample.

9. The interferometer system of claim 8, said polarization adjusting device being operable selectively to determine the polarization states of light directed to the sample.

10. An interferometer system having polarization sensitivity, comprising:
a reference arm providing a delay line for electromagnetic energy, where the reference arm is absent addressable polarization selecting components;
a sample arm providing a path for incident electromagnetic energy having prescribed polarization characteristics to a sample, said sample arm including a polarizer and a polarization adjusting device that is operable to modulate continuously such polarization; and
a detector arranged to detect electromagnetic energy from the delay line and from the sample.

11. A method of making polarization sensitive optical coherence tomography measurements, said method comprising:
in a reference arm, providing a delay line for electromagnetic energy, where the reference arm is absent addressable polarization selecting components;
in a sample arm, providing a path for incident electromagnetic energy having prescribed polarization characteristics to a sample, selectively modulating the polarization to determine the polarization states of the electromagnetic energy directed to the sample; and
detecting electromagnetic energy from the delay line and from the sample.

12. A method of making polarization sensitive optical coherence tomography measurements, said method comprising:
in a reference arm, providing a delay line for electromagnetic energy, where the reference arm is absent addressable polarization selecting components;
in a sample arm, providing a path for incident electromagnetic energy having prescribed polarization characteristics to a sample, continuously modulating polarization of electromagnetic energy directed to the sample; and
detecting electromagnetic energy from the delay line and from the sample.

* * * * *

UNITED STATES PATENT AND TRADEMARK OFFICE
CERTIFICATE OF CORRECTION

| | | |
|---|---|---|
| PATENT NO. | : 7,826,059 B2 | Page 1 of 1 |
| APPLICATION NO. | : 10/055282 | |
| DATED | : November 2, 2010 | |
| INVENTOR(S) | : Roth et al. | |

It is certified that error appears in the above-identified patent and that said Letters Patent is hereby corrected as shown below:

Specification:

In column 6, line 3, delete "proportion" and insert --proportional--.

In column 6, line 37, delete "setting of °,90°, and 135°," and insert --setting of 45°, 90°, and 135°.--.

Signed and Sealed this
Twenty-second Day of February, 2011

David J. Kappos
*Director of the United States Patent and Trademark Office*